United States Patent
O'Prey et al.

(10) Patent No.: US 10,335,021 B2
(45) Date of Patent: *Jul. 2, 2019

(54) ENDOSCOPE WIPER BLADE CLEANER

(71) Applicant: Covidien LP, Mansfield, MA (US)

(72) Inventors: Cormac O'Prey, Bishop Stortford (GB); Charlotte Adele Clark, Cambridge (GB); Alistair Ian Fleming, Cambridge (GB)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/708,931

(22) Filed: Sep. 19, 2017

(65) Prior Publication Data

US 2018/0008136 A1    Jan. 11, 2018

Related U.S. Application Data

(63) Continuation of application No. 13/245,022, filed on Sep. 26, 2011, now Pat. No. 9,763,567.

(60) Provisional application No. 61/394,819, filed on Oct. 20, 2010.

(51) Int. Cl.
*A61B 1/00* (2006.01)
*A61B 1/12* (2006.01)
*A61B 1/313* (2006.01)

(52) U.S. Cl.
CPC ............ *A61B 1/126* (2013.01); *A61B 1/0014* (2013.01); *A61B 1/00087* (2013.01); *A61B 1/00091* (2013.01); *A61B 1/00101* (2013.01); *A61B 1/00135* (2013.01); *A61B 1/3132* (2013.01)

(58) Field of Classification Search
CPC ..... A61B 1/126; A61B 1/3132; A61B 1/0014; A61B 1/00087; A61B 1/00101; A61B 1/00091; A61B 1/00135
See application file for complete search history.

(56) References Cited

U.S. PATENT DOCUMENTS

| | | |
|---|---|---|
| 4,281,646 A | 8/1981 | Kinoshita |
| 4,919,113 A | 4/1990 | Sakamoto et al. |
| 4,941,872 A | 7/1990 | Felix et al. |
| 5,207,213 A | 5/1993 | Auhll et al. |
| 5,274,874 A | 1/1994 | Cercone et al. |
| 5,313,934 A | 5/1994 | Wiita et al. |
| 5,337,730 A | 8/1994 | Maguire |
| 5,339,800 A | 8/1994 | Wiita et al. |
| 5,392,766 A | 2/1995 | Masterson et al. |
| 5,400,767 A | 3/1995 | Murdoch |

(Continued)

FOREIGN PATENT DOCUMENTS

| | | |
|---|---|---|
| DE | 102008059633 A1 | 6/2010 |
| EP | 1210904 A2 | 6/2002 |

(Continued)

OTHER PUBLICATIONS

European Search Report from EP Application No. EP 12154377.1 dated May 25, 2012 (6 pages).

(Continued)

*Primary Examiner* — Timothy J Neal

(57) ABSTRACT

A minimally invasive surgical instrument including a viewing instrument and a wiper mechanism configured and adapted to clean a lens of the viewing instrument. The wiper mechanism includes a wiper that is configured and adapted to contact and translate across a surface of the lens. An actuator moves the wiper across the lens to clean the lens.

16 Claims, 4 Drawing Sheets

(56) References Cited

U.S. PATENT DOCUMENTS

| | | |
|---|---|---|
| 5,514,084 A | 5/1996 | Fisher |
| 5,518,502 A | 5/1996 | Kaplan et al. |
| 5,630,795 A | 5/1997 | Kuramoto et al. |
| 5,735,792 A | 4/1998 | Vanden Hoek et al. |
| 5,842,971 A | 12/1998 | Yoon |
| 5,931,833 A | 8/1999 | Silverstein |
| 5,944,654 A | 8/1999 | Crawford |
| 6,354,992 B1 | 3/2002 | Kato |
| 6,387,044 B1 | 5/2002 | Tachibana et al. |
| 6,682,165 B2 | 1/2004 | Yearout |
| 6,755,782 B2 | 6/2004 | Ogawa |
| 6,923,759 B2 | 8/2005 | Kasahara et al. |
| 7,300,445 B2 | 11/2007 | Adams |
| 7,316,683 B2 | 1/2008 | Kasahara et al. |
| 7,339,341 B2 | 3/2008 | Oleynikov et al. |
| 7,530,984 B2 | 5/2009 | Sonnenschein et al. |
| 7,596,828 B2 | 10/2009 | Evdokimo |
| 7,922,701 B2 | 4/2011 | Buchman |
| 7,959,561 B2 | 6/2011 | Akui et al. |
| 9,763,567 B2 | 9/2017 | O'Prey et al. |
| 2002/0065450 A1 | 5/2002 | Ogawa |
| 2003/0073955 A1 | 4/2003 | Otawara |
| 2006/0293559 A1 | 12/2006 | Grice et al. |
| 2007/0149850 A1 | 6/2007 | Spivey et al. |
| 2007/0208220 A1 | 9/2007 | Carter |
| 2007/0208221 A1 | 9/2007 | Kennedy et al. |
| 2007/0213667 A1 | 9/2007 | Prusmack |
| 2007/0282253 A1 | 12/2007 | Sasaki |
| 2007/0282356 A1 | 12/2007 | Sonnenschein et al. |
| 2007/0299310 A1 | 12/2007 | Phillips |
| 2008/0015618 A1 | 1/2008 | Sonnenschein et al. |
| 2008/0188715 A1 | 8/2008 | Fujimoto |
| 2008/0319266 A1 | 12/2008 | Poll et al. |
| 2009/0049627 A1 | 2/2009 | Kritzler |
| 2009/0105543 A1 | 4/2009 | Miller et al. |
| 2009/0112065 A1 | 4/2009 | Harrel |
| 2009/0240111 A1 | 9/2009 | Kessler et al. |
| 2009/0270686 A1 | 10/2009 | Duke et al. |
| 2009/0287052 A1 | 11/2009 | Amos et al. |
| 2010/0030031 A1 | 2/2010 | Goldfarb et al. |
| 2010/0174144 A1 | 7/2010 | Hsu et al. |
| 2010/0225753 A1 | 9/2010 | Karasawa et al. |
| 2011/0230716 A1 | 9/2011 | Fujimoto |

FOREIGN PATENT DOCUMENTS

| | | |
|---|---|---|
| EP | 1323373 A2 | 7/2003 |
| EP | 1911409 A1 | 4/2008 |
| JP | 2005040184 A | 2/2005 |
| JP | 2005052229 A | 3/2005 |
| JP | 2007105314 A | 4/2007 |
| JP | 2007130167 A | 5/2007 |
| JP | 2008132282 A | 6/2008 |
| JP | 2008279202 A | 11/2008 |
| JP | 2010022758 A | 2/2010 |
| WO | 2008153841 A2 | 12/2008 |

OTHER PUBLICATIONS

European Search Report dated Oct. 10, 2012 for copending European Application No. 12154377.

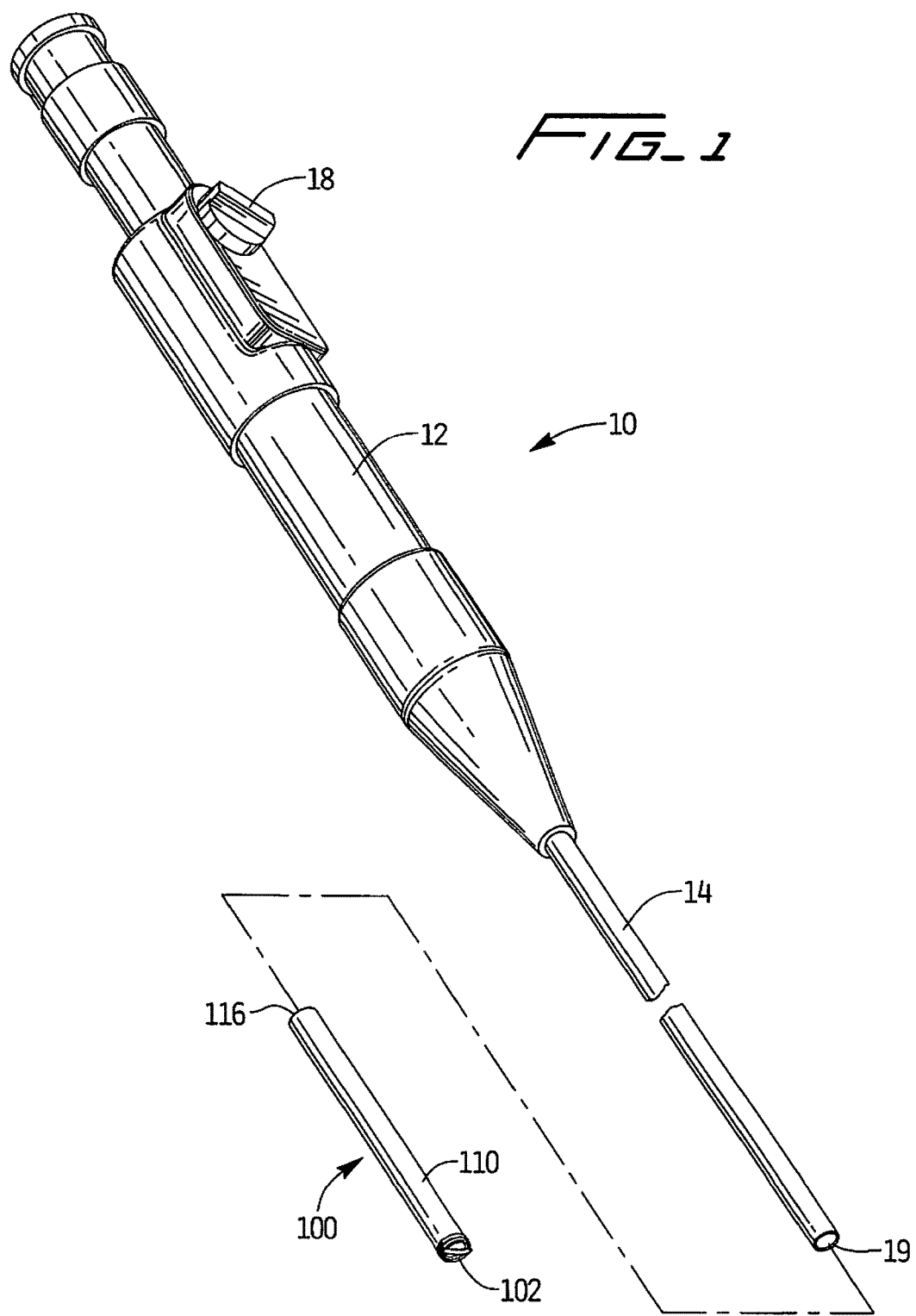
FIG_1

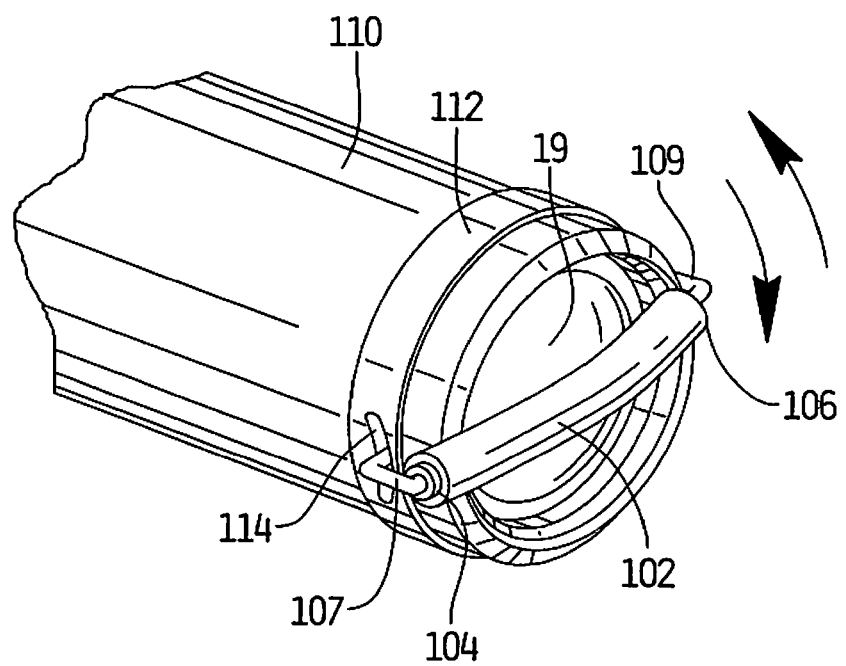

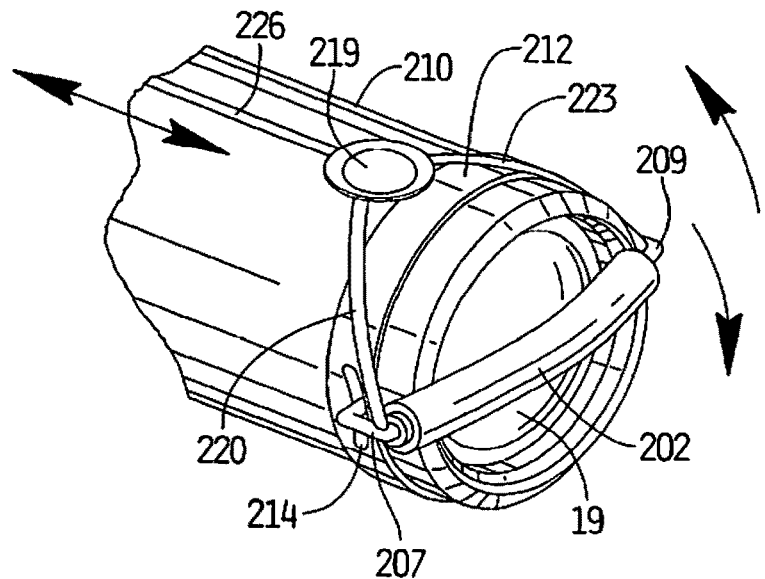
FIG_3
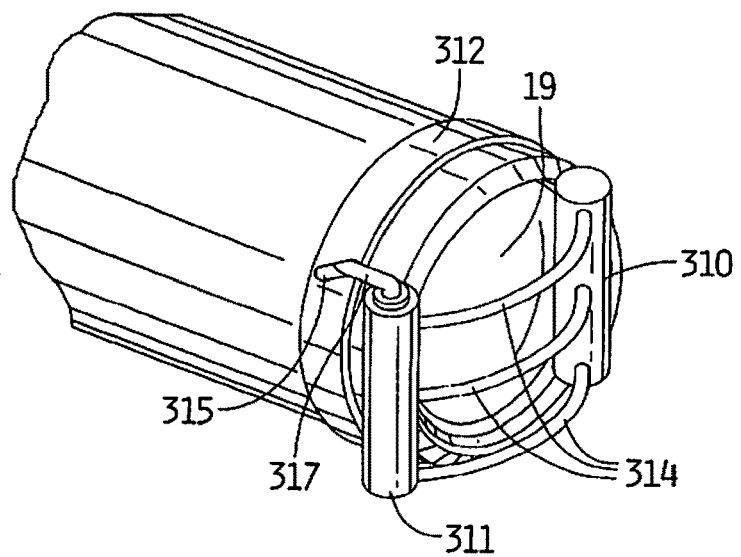
FIG_4

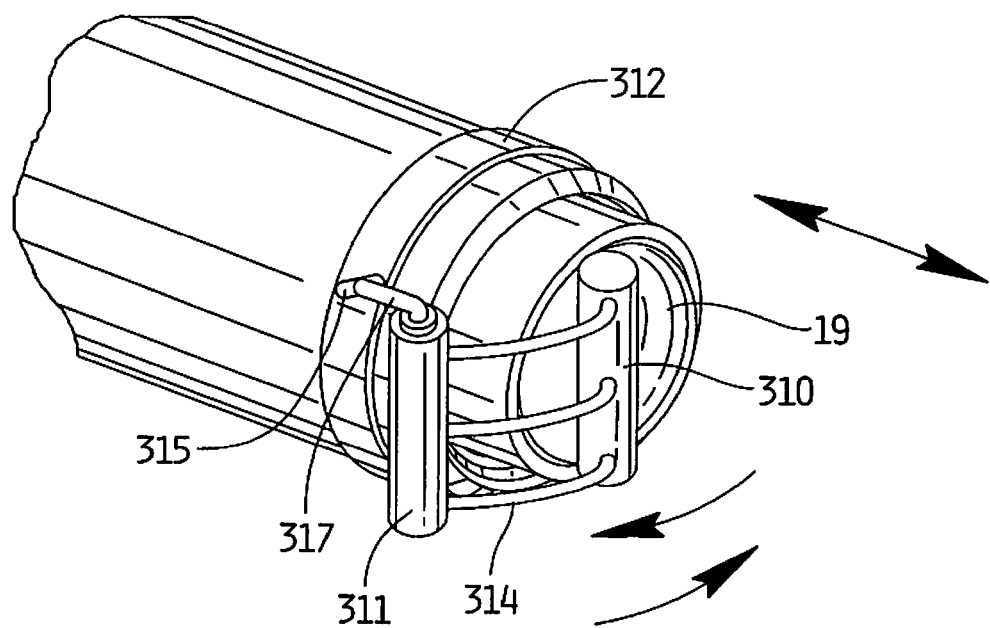

ENDOSCOPE WIPER BLADE CLEANER

CROSS-REFERENCE TO RELATED APPLICATIONS

This application is a continuation of U.S. patent application Ser. No. 13/245,022, filed Sep. 26, 2011, now U.S. Pat. No. 9,763,567, which claims priority from Provisional Application Ser. No. 61/394,819, filed Oct. 20, 2010, the entire contents of which are incorporated herein by reference.

BACKGROUND

Technical Field

The present disclosure relates to a cleaning apparatus configured to remove debris from the lens of a minimally invasive viewing instrument.

Background of Related Art

Minimally invasive surgery has become increasingly popular in recent years. Minimally invasive surgery eliminates the need to cut a large incision in a patient, thereby reducing discomfort, recovery time, and many of the deleterious side effects associated with traditional open surgery. Minimally invasive viewing instruments, e.g., laparoscopes and endoscopes, are optic instruments to facilitate the viewing of internal tissues and/or organs.

Laparoscopic surgery involves the placement of a laparoscope in a small incision in the abdominal wall of a patient, to view the surgical site. Endoscopic surgery involves the placement of an endoscope in a naturally occurring orifice, e.g., mouth, nose, anus, urethra, and vagina, to view the surgical site. Other minimally invasive surgical procedures include video assisted thoracic surgery and cardiovascular surgery etc. conducted through small incisions between the ribs. These procedures also utilize scopes to view the surgical site.

A typical minimally invasive viewing instrument, e.g., a laparoscope or an endoscope, includes a housing, an elongated lens shaft extending from one end of the housing, and a lens that is provided in the distal end of the lens shaft. A camera viewfinder extends from the other end of the housing. A camera is connected to the housing and transmits images sighted through the lens to a television monitor on which the images are displayed. During a surgical procedure, the distal end portion of the lens shaft is extended into the patient, while the proximal end portion of the lens shaft, the housing and the camera viewfinder remain outside the patient. In this manner, the laparoscope/endoscope is positioned and adjusted to view particular anatomical structures in the surgical field on the monitor.

During insertion of an endoscope or a laparoscope into the body and during the surgical procedure, debris, e.g., organic matter and moisture, may be deposited on the lens of the scope. The buildup of debris and condensation on the lens impairs visualization of the surgical site, and often necessitates cleaning of the lens.

SUMMARY

The present disclosure is generally related to an instrument for cleaning the lens of a medical viewing instrument, such as an endoscope, during a minimally invasive surgical procedure. In one aspect, the present disclosure provides a minimally invasive surgical instrument comprising a viewing instrument including a lens and having a longitudinal axis and a wiper mechanism attachable to the viewing instrument prior to introducing the viewing instrument into a body of a patient. The wiper mechanism includes a wiper configured and adapted to contact and translate across a surface of the lens. An actuator is positioned at a proximal portion of the viewing instrument and is actuable to move the wiper from an initial position across the lens to clean the lens.

In some embodiments, the wiper is operatively connected to the actuator by at least one elongated member, which can be flexible. The wiper can be biased toward the initial position.

In some embodiments, the wiper includes a substantially cylindrical member having a longitudinal axis, the longitudinal axis being substantially transverse to the longitudinal axis of the viewing instrument. In some embodiments, the wiper mechanism includes first and second spaced apart substantially cylindrical members, the members connected by at least one connector. The substantially cylindrical member(s) can have first and second opposing ends, and a control mechanism can be attached to the first and second opposing ends.

An elongated member can be provided operably connected to the actuator at a proximal end and operably connected to the wiper at the distal end and translatable to move the wiper across the lens. The elongated member in some embodiments is a control wire extending along an outer surface of the viewing instrument. The control wire can be clipped to an outer surface of the viewing instrument. The elongated member can be spring biased to maintain the wiper in the position offset from a central axis of the viewing instrument, thereby removed from a central viewing area of the lens.

The wiper mechanism can include a collar mountable at a distal end of the viewing instrument and the wiper can be movably connected to the collar.

In another aspect, the present disclosure provides a surgical instrument comprising a wiper mechanism adapted to be secured to a viewing instrument having a lens. The wiper mechanism includes a first substantially cylindrical member having a longitudinal axis transverse to a longitudinal axis of the viewing instrument. The substantially cylindrical member is movable across the lens of the viewing instrument to clean the lens.

In some embodiments, the wiper mechanism includes a second substantially cylindrical member and the substantially cylindrical members are spaced apart and connected by at least one connector.

In some embodiments, the wiper mechanism is connected to a collar mounted to the viewing instrument and a control member extends adjacent an outer surface of the viewing instrument and is actuable to move at least the first substantially cylindrical member across the lens.

The wiper in some embodiments can also have a spray attachment for cleaning the lens connected to a pressurized fluid reservoir.

In some embodiments, a sheath having an interior dimension to receive a portion of the viewing instrument is provided and the first cylindrical member is connected to the sheath. In some embodiments, an arm extends into a portion of the cylindrical member. The sheath can include a slot to receive the arm.

These and other features of the present disclosure will be more fully described with reference to the appended figures.

BRIEF DESCRIPTION OF THE DRAWINGS

By way of description only, embodiments of the present disclosure will be described with reference to the accompanying drawings, in which:

FIG. 1 is a perspective view of a surgical viewing instrument and wiper mechanism in accordance with an embodiment of the present disclosure;

FIG. 2 is an enlarged perspective view of the distal end portion of the surgical viewing instrument of FIG. 1;

FIG. 3 is an enlarged perspective view of the distal end portion of a surgical viewing instrument having an alternate embodiment of the wiper mechanism mounted thereto;

FIG. 4 is an enlarged perspective view of the distal end portion of a surgical viewing instrument having another alternate embodiment of the wiper mechanism mounted thereto; and FIG. 5 illustrates the wiper of FIG. 4 being moved across the scope lens.

DETAILED DESCRIPTION

An endoscope typically includes an endoscope housing or body which can be rigid or flexible, depending on its surgical application. A camera viewfinder, e.g. an eyepiece, is located at a proximal (imaging) end of the scope housing. A lens is provided at the distal end of the scope body.

In typical use of the endoscope, the viewfinder is adapted to sight images of a surgical field in the patient, e.g. an abdominal cavity, thoracic cavity, etc., as the position of the scope is adjusted to view a particular anatomical structure or structures in the surgical field. The camera is adapted to receive images of the surgical field sighted through the lens and transmit the images to an external monitor that is connected to the camera and on which the images of the surgical field are displayed. That is, a visual display device is operatively connected to the eyepiece to convert the optical signal into a video signal to produce a video image on the monitor (or for storage on select media). Accordingly, the monitor enables a surgical team to view the anatomical structure or structures in the surgical field inside the patient as the surgical procedure is carried out using minimally invasive or endoscopic surgical instruments. Throughout the surgical procedure, condensation, smoke particles, and biological tissue or matter has a tendency to contact and build up on the lens of the scope. This tends to obscure the images of the surgical field as they are displayed on the monitor.

The instrument of the present disclosure enables cleaning of the scope lens during the surgical procedure to maintain a clear image without having to remove the scope from the patient's body.

Particular embodiments of the present disclosure will be described herein with reference to the accompanying drawings. In the figures and in the description that follows, in which like reference numerals identify similar or identical elements, the term "proximal" will refer to the end of the instrument that is closer to the operator during use, while the term "distal" will refer to the end that is further from the operator during use.

The present disclosure is directed to wiper mechanisms which can be attachable to a conventional viewing instrument, e.g. a laparoscope or endoscope, The wiper mechanism includes one or more roller or wiper members movable across the lens of the scope to clean the lens. In some embodiments, the roller member(s) are moved by a remotely positioned actuator. In other embodiments, the roller member(s) are moved across the lens by advancement of the scope lens into contact with the roller member(s). An injection port such as a spray head can also be provided to inject, e.g. spray, fluid onto the lens. That is, the wiper can be part of an elongated sheath containing a fluid conduit which delivers fluid to the scope lens. In an alternate embodiment, partial retraction of the scope can facilitate part of the cleaning cycle to actuate part of the cleaning element.

A conventional endoscope is illustrated in FIG. 1 by way of example and designated by reference numeral 10. The scope 10 has a handle 12 and an elongated tubular shaft 14 extending distally from the handle 12 and terminating in a lens 19. The tubular shaft can be rigid, semi-rigid or flexible. In the embodiment of FIG. 1, a wiper mechanism 100 including a sheath 110 is positioned over the scope lens 19 and a portion of the shaft 14. The sheath 110 can be rigid, semi-rigid or flexible to accommodate a flexible elongated shaft of an endoscope. The sheath has an interior dimension for receipt of the scope. In alternate embodiments, the wiper mechanism is attached to a collar mounted over a distal tip of the scope.

Turning first to the embodiment of FIGS. 1 and 2, wiper mechanism 100 includes a wiper in the form of a substantially cylindrical roller member 102 having first and second opposed ends 104, 106. The roller member 102 has a longitudinal axis (slightly curved) which is substantially transverse to a longitudinal axis of the scope 10. The wiper mechanism 100 is connected to sheath 110 mounted on the distal portion of the scope 10. The sheath 110 includes a collar or ring 112 having a slot 114 formed therein on each side. The sheath can be configured of different lengths to cover different lengths of the scope 10.

Arms 107, 109 support roller member 102 on opposing ends thereof, and bend inwardly to extend through radially positioned slots 114 of collar 112. The arms 107, 109 can be in the form of a rod, tube, wire, etc. and can be integrally formed so they extend as one unit within the interior of roller member 102. Alternatively, a separate connecting member can extend through or be positioned within the interior of roller member 102 to join the two arms 107, 109. The arms 107, 109 are connected to an actuating member such as a rod or wire (not shown) that extends within the sheath 110 and exits from the proximal end 116 of sheath 110 and alongside (not shown) the outer surface of the scope 10. The rod or wire can be clipped to the side of the scope 10 (not shown). The rod or wire is operatively connected to a lever 18 or other control member (actuator) for movement of the rod or wire to actuate the roller 102.

The roller member 102 is preferably spring biased to a first position removed from the central viewing area of the lens 19. In use, the actuating rod or wire is pulled proximally by actuation of the control (actuating) member, thereby moving the arms 107, 109 within the slots 114 to rotate the roller member 102 across the scope lens 19 to clean the lens. The roller member in this and the other embodiments described herein can be composed of a material to wipe the lens or alternatively, the roller member of this and other embodiments can be composed of metal or other material and covered with a material to wipe the scope lens.

In the alternate embodiment of FIG. 3, the roller member 202 of wiper mechanism 200 is similar to roller member 102 of FIG. 2, and has arms 207, 209 similar to arms 107, 109. The wiper mechanism 200 differs from wiper mechanism 100 in that instead of an actuating member extending through the sheath, support members 220, 223 are attached to arms 207, 209, and are in a Y-configuration, clipped at disk 219 to the outer surface of the sheath 210, and preferably clipped to the scope as well. Arms 207, 209 extend through radially extending slots 214 in collar or ring 212 to connect the roller member 202 to the collar 212. Proximal retraction of the actuating member 226, which can be in the form of a wire, rod or drawstring, for example, pulls support members 220, 223 proximally to rotate the roller member 202 across the lens 19. As with the embodiment of FIG. 2, the roller 202 is preferably spring biased to be removed from the viewing area of the scope lens 19 and pulling of the wire 226 overcomes the bias to rotate the roller member across the lens, with the arms 207, 209 traveling within slots 214.

In the embodiments of FIGS. 1-3, a manual lever, e.g. lever 18 of FIG. 1, can be attached to the actuating member (actuator) to manually move the actuating member between proximal and distal positions to move the wiper mechanism from a position adjacent the lens (away from the viewing area) before cleaning to a position across the lens for cleaning. The manual lever can be fixed to the body of the scope near the handle for accessibility and the lever can be spring biased to a position maintaining the wiper away from the central viewing area of the lens.

As an alternative to an actuator, e.g. a lever, actuable at a proximal end of the scope to move the roller member(s), the roller member(s) can be moved across the scope lens by movement of the scope itself. This is shown in the embodiment of FIGS. 4 and 5.

In the embodiment of FIGS. 4 and 5, two wipers in the form of substantially cylindrical roller members 310, 311 are provided. Roller members 310, 311 are connected by at least one connector and in the illustrated embodiment are connected by three spaced apart connectors 314. Connectors 314 are arcuate and extend across the lens 19 of the scope. Movement of the roller members 310, 311 across the lens can be appreciated by comparing FIGS. 4 and 5. In FIG. 5, the roller member 310 is rotated across the viewing lens 19 as the scope and lens are extended distally through the sheath and contact the roller 310, thereby causing it to rotate across the lens 19. As the viewing instrument is retracted, the wiper 300 translates back to the initial position. This can be achieved for example by the wiper mechanism being biased to the initial position by a spring or other mechanism. The rollers 310, 311 are attached to collar 312 via arm 317 extending from roller 311 into slot 315 of collar 312. A second arm can optionally extend from roller 310 into a second slot in the collar.

The wiper mechanisms described herein may be permanently or removably coupled to the distal end of a sheath such as sheath 110 which is mounted over the scope. A ring or collar, such as collar 112, may be coupled to the distal end of the sheath, for example, by frictional, adhesive, or magnetic means. The collar can include guide slots for the arms, which are operatively connected to the roller. Actuation of the roller to translate across the lens 19 can be achieved using known mechanical or electro-mechanical means. In addition, the actuation may occur automatically, intermittently, and/or in response to certain conditions.

To facilitate unobstructed viewing through the lens 19, the rollers can be moved in either direction beyond the radius of the lens 19.

The rollers disclosed herein facilitate the cleaning and/or drying of the lens. The rollers may be formed from materials including, but not limited to, a polymer, a fabric, a rubber, or a sponge-like material. Alternatively, the rollers can be covered with such material. The rollers may be semi-rigid and may flex to conform to the shape of the lens 19 to facilitate maximum contact between the lens 19 and the rollers. Moreover, the rollers may be substantially cylindrically shaped to facilitate rolling.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument comprising:
a viewing instrument including a lens; and
a wiper mechanism attachable to the viewing instrument, the wiper mechanism including:
a sheath configured to receive the lens therethrough; and
first and second cylindrical members operatively coupled to the sheath, wherein the first cylindrical member is rotatable about a longitudinal axis of the second cylindrical member extending along the length of the second cylindrical member when the lens extends distally through the sheath such that the first cylindrical member wipes the lens.

2. The surgical instrument according to claim 1, wherein the wiper mechanism further includes a connector connecting the first and second cylindrical members.

3. The surgical instrument according to claim 2, wherein the connector is arcuate.

4. The surgical instrument according to claim 2, wherein the first cylindrical member is formed of at least one of a polymer, a fabric, or a rubber.

5. The surgical instrument according to claim 1, wherein the first cylindrical member is transitionable between a first position in which the first and second cylindrical members are diametrically spaced apart relative to a surface of the lens, and a second position in which the first cylindrical member is translated across the surface of the lens.

6. The surgical instrument according to claim 5, wherein the first and second cylindrical members are parallel to each other in the first position.

7. The surgical instrument according to claim 5, wherein the first cylindrical member is biased toward the first position.

8. The surgical instrument according to claim 1, wherein the wiper mechanism includes a collar mounted at a distal end of the sheath, the collar supporting the first and second cylindrical members.

9. The surgical instrument according to claim 1, wherein the longitudinal axis of the second cylindrical member is laterally spaced apart from a longitudinal axis defined by the first cylindrical member.

10. A surgical instrument comprising:
a wiper mechanism operatively associated with a viewing instrument having a lens, the wiper mechanism including:
first and second cylindrical members, the first cylindrical member pivotable about a longitudinal axis of the second cylindrical member as the first cylindrical member moves diametrically across the lens of the viewing instrument, the first and second cylindrical members transitionable from a first position in which the first and second cylindrical members are spaced apart relative to a surface of the lens, and a second position in which the first cylindrical member is displaced across the surface of the lens.

11. The surgical instrument according to claim 10, wherein the first and second cylindrical members are diametrically spaced apart with respect to the surface of the lens when the first and second cylindrical members are in the first position.

12. The surgical instrument according to claim 10, further comprising a sheath having an interior dimension to receive a portion of the viewing instrument, the second cylindrical member coupled to the sheath.

13. The surgical instrument according to claim 10, wherein the first and second cylindrical members are biased toward the first position.

14. The surgical instrument according to claim 10, wherein the first and second cylindrical members are parallel to each other in the first position.

15. The surgical instrument according to claim 10, wherein the wiper mechanism further includes a connector connecting the first and second cylindrical members.

16. The surgical instrument according to claim 15, wherein the connector extends diametrically over the surface of the lens when the first and second cylindrical members are in the first position.

* * * * *